(12) United States Patent
Freedman

(10) Patent No.: US 6,838,875 B2
(45) Date of Patent: Jan. 4, 2005

(54) PROCESSING NMR DATA IN THE PRESENCE OF COHERENT RINGING

(75) Inventor: Robert Freedman, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 46 days.

(21) Appl. No.: 10/142,558

(22) Filed: May 10, 2002

(65) Prior Publication Data

US 2003/0210043 A1 Nov. 13, 2003

(51) Int. Cl.$^7$ ................................................. G01V 3/00
(52) U.S. Cl. ........................................................ 324/303
(58) Field of Search ......................................... 324/303

(56) References Cited

U.S. PATENT DOCUMENTS

| | | | |
|---|---|---|---|
| 4,480,227 A | * 10/1984 | Brown | 324/303 |
| 5,291,137 A | 3/1994 | Freedman | |
| 5,486,762 A | * 1/1996 | Freedman et al. | 324/303 |
| 6,049,205 A | * 4/2000 | Taicher et al. | 324/303 |
| 6,069,477 A | * 5/2000 | Chen et al. | 324/303 |
| 6,084,408 A | * 7/2000 | Chen et al. | 324/303 |
| 6,121,774 A | 9/2000 | Sun et al. | |
| 6,166,543 A | 12/2000 | Sezginer et al. | |
| 6,184,681 B1 | * 2/2001 | Heidler et al. | 324/303 |
| 6,229,308 B1 | * 5/2001 | Freedman | 324/303 |
| 6,232,778 B1 | 5/2001 | Speier et al. | |
| 6,255,818 B1 | 7/2001 | Heaton et al. | |
| 6,344,744 B2 | * 2/2002 | Taicher et al. | 324/303 |
| 6,388,441 B1 | * 5/2002 | Chen | 324/303 |
| 6,392,409 B1 | * 5/2002 | Chen | 324/303 |
| 6,400,147 B1 | 6/2002 | Toufaily et al. | |
| 6,452,389 B1 | * 9/2002 | Edwards | 324/303 |
| 6,459,992 B1 | 10/2002 | Freedman et al. | |
| 6,462,542 B1 | * 10/2002 | Venkataramanan et al. | |
| 6,498,484 B1 | 12/2002 | Sun et al. | |
| 6,518,757 B1 | 2/2003 | Speier | |
| 6,522,137 B1 | 2/2003 | Sun et al. | |
| 6,522,138 B2 | 2/2003 | Heaton | |
| 6,525,534 B2 | * 2/2003 | Akkurt et al. | 324/303 |
| 6,531,868 B2 | * 3/2003 | Prammer | 324/303 |
| 6,534,980 B2 | 3/2003 | Toufaily et al. | |
| 6,559,638 B1 | 5/2003 | Adelerhof | |
| 6,559,639 B2 | * 5/2003 | Minh et al. | 324/303 |
| 6,570,382 B1 | * 5/2003 | Hurlimann et al. | 324/303 |
| 6,573,716 B2 | 6/2003 | Toufaily et al. | |
| 2001/0033163 A1 | 10/2001 | Sigal et al. | |

FOREIGN PATENT DOCUMENTS

WO    WO 02/33444 A1    4/2002

OTHER PUBLICATIONS

McKeon et al., An Improved NMR Tool Design for Faster Logging, pp. 1–14.
Freedman et al., Measurement of Total NMR Porosity Adds New Value to NMR Logging, SPWLA 38$^{th}$ Annual Logging Symposium , Jun. 15–18, 1997, pp. 1–14.
Sigal et al., A Method for Enhancing the Vertical Resolution of NMR Logs, SPE International, Oct. 1–4, 2000, pp. 733–743.
Akkurt et al., The Key to Improving the Vertical Resolution of Multi–Frequency NMR Logging Tools, SPWLA 42$^{nd}$ Annual Logging Symposium , Jun. 17–20, 2001.

* cited by examiner

*Primary Examiner*—Christopher W. Fulton
*Assistant Examiner*—Dixomara Vargas
(74) *Attorney, Agent, or Firm*—Kevin P. McEnaney; Brigitte L. Echols; John Ryberg

(57) ABSTRACT

A method for processing Nuclear magnetic resonance (NMR) well logging data in the presence of coherent transient signals and offsets is disclosed. The method comprises the addition of R and X-Channel transients and offsets to the relaxation model appropriate for a user selected pulse sequence. The effects of the ringing and offsets are automatically compensated for by fitting R and X-Channel spin-echo data to the relaxation model.

34 Claims, 3 Drawing Sheets

PROCESSING NMR DATA IN THE PRESENCE OF COHERENT RINGING

CROSS REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

This invention relates to techniques for determining characteristics of earth formations surrounding a borehole and, more particularly, to nuclear magnetic resonance borehole logging that utilizes data processing to improve performance

BACKGROUND OF THE INVENTION

A widely used technique for acquiring nuclear magnetic resonance (NMR) data both in the laboratory and in well logging, uses an RF pulse sequence known as the CPMG (Carr-Purcell-Meiboom-Gill) sequence. As is known, after a wait time that precedes each pulse sequence, known as polarization time, a ninety degree pulse that rotates the magnetization to the x-y plane. The spins begin to precess around $B_0$ and dephase due to inhomogeneity in the magnetic field and spin-spin interactions. After a certain time delay, a one hundred eighty degree pulse is applied to cause the spins which are dephasing in the transverse plane to refocus. Refocusing leads to an echo that is detected by the NMR instrument. By repeated application of one hundred eighty degree pulses, a series of "spin echoes" appear, and the train of echoes is measured and processed.

It is recognized that "ringing" is a problem encountered when using pulsed NMR techniques. Ringing noise can arise, for example, from electromagnetic (EM) cross-talk or magneto-acoustic vibrations in the transmitting and/or receiving antennas or circuits. Noise coherent with the pulse sequence always exist in raw NMR data and must be taken into account in order to extract accurate NMR signal parameters from the raw data. The ringing noise is in addition to random thermal noise that always exists in NMR data. Signal averaging of raw data sets can reduce the random noise but cannot reduce coherent noise. The NMR raw data in general consist of NMR signal, ringing noise, and random noise. The ringing noise usually consists of a constant or weakly time-dependent offset plus a time-dependent transient. The transient rapidly decays to zero and is significant only at early times. For CPMG and similar spin-echo generating pulse sequences the transient is produced by the 90-degree pulse and usually has the same phase as the signal. The transient typically persists for a relatively few echoes whereas the offsets are present on all echoes.

The ringing offsets are assumed to be independent of the phase of the 90-degree radio-frequency (rf) pulse that creates the transverse magnetization in CPMG and similar pulse sequences. One prior art method for removing the offset signal involves acquisition of two phase alternated CPMG spin-echo sequences using 90-degree pulses that are phase shifted with respect to one another by 180 degrees. The phase shift of the 90-degree pulse causes the reversal of the sign of the NMR signal and the transient signal. The offset remains unchanged. Therefore subtracting the two phase-alternated pairs (PAP) eliminates the offset. This method is widely used in NMR laboratory spectrometers as well as in NMR well-logging tools. One of the drawbacks of the PAPs method is that it requires combining two acquisitions. This limits the vertical resolution for well-logging measurements made in non-overlapping measurement mode to twice the antenna aperture (see e.g., McKeon et al. SPWLA Transactions, 1999). The PAP method can also fail to satisfactorily remove the offset if it changes significantly from one acquisition to the next due, for example, to changes in the conductivity of the rock formation that are not fully compensated for by the gain corrections that are separately applied to each of the CPMGs in a PAP. Another limitation of the PAP method is that it only removes the offset and does not remove or reduce the effects of the transient noise, i.e., the 90-degree ringing.

Another approach (U.S. Pat. No. 6,121,774) for removing ringing from a pulse sequence is to acquire NMR raw data that contains only the ringing signals, i.e., the NMR signal is not present. The ringing signals can be recorded and used to correct the raw data. For example, one approach proposes a method whereby "spoiling pulses" are applied at the end of each CPMG in order to cancel the NMR signal so that ringing signals can be recorded. The ringing signals are averaged to reduce random noise and then subtracted from each echo in the CPMG.

Another method (Sigal et al. in SPE Paper No. 63215) for removing the offset signal from NMR well-logging data has been proposed to estimate the offset (also referred to as the bias) signal by adding adjacent CPMG echo trains that are acquired with 90-degree pulses differing in phase by 180 degrees. The offset is then subtracted from each echo to obtain bias corrected NMR data. This method of estimating bias is most appropriate when the formation signal remains constant during the acquisition of two adjacent CPMGs. However, in practice the formation properties and therefore the formation signal changes from one acquisition to another. Furthermore the method does not effectively remove transient ringing. The prior art methods attempt to remove the ringing from the raw data prior to processing the data in order to extract the NMR signal.

SUMMARY OF INVENTION

Nuclear magnetic resonance (NMR) data is processed to obtain an output substantially eliminate the effects of coherent transient signals and offsets that contaminate NMR spin-echo signals. Raw data received from NMR measurements are fitted to a relaxation model using an iterative process. The relaxation model consists of a set of variables that represent the NMR signal contribution appropriate for a specific formation fluid model and typical noise components. The noise components further consist of a time dependent transient noise component and a generally constant offset noise component.

DETAILED DESCRIPTION OF THE INVENTION

Figure 1:
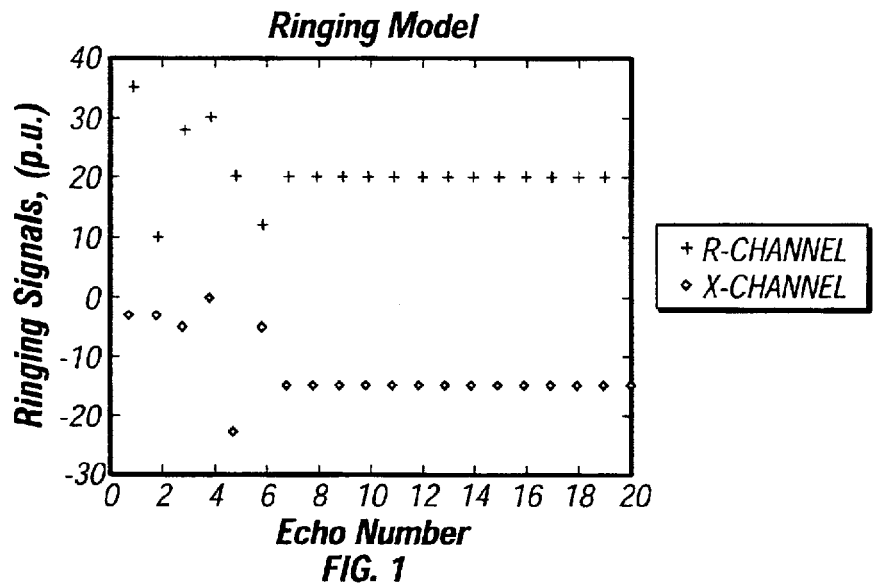
FIG. 1 shows hypothetical transient and offset noise signals in the R and X-channel of a typical CPMG pulse sequence.

The disclosed subject matter is a signal processing method that provides accurate estimation of NMR signal parameters in the presence of offsets and transient ringing. Methods according to the disclosed processing schemes improves the vertical resolution of NMR logs recorded by well-logging tools. Specifically, the disclosed methods account for the effects of ringing as part of the processing.

According to a disclosed embodiment, ringing elimination is based on fitting raw R and X-channel spin-echo amplitudes to a theoretical model that includes an appropriate NMR relaxation model plus coherent ringing and random noise. The coherent ringing model consists of a constant offset plus an arbitrary time-dependent transient. The ringing is assumed to be different in the two signal detection channels. It is shown that the transient, offset, and NMR parameters (e.g., T2-distributions) can be simultaneously estimated from the raw data.

Consider a relaxation model for which the raw R and X-channel spin-echo amplitudes have the form:

$$\tilde{R}_j^p = \sum_{l=1}^{N_S} a_{l,r} \exp\left(-\frac{t_{j,p}}{T_{2,l}}\right) f_{l,p}(\xi) + \tilde{N}_{j,p}^r + \Delta_{j,p}^r \quad (1)$$

and, $$\tilde{X}_j^p = \sum_{l=1}^{N_S} a_{l,x} \exp\left(-\frac{t_{j,p}}{T_{2,l}}\right) f_{l,p}(\xi) + \tilde{N}_{j,p}^x + \Delta_{j,p}^x. \quad (2)$$

Equations (1) and (2) represent a rock formation NMR model where the signal is a multi-exponential decay with a distribution of T2 relaxation times. $\tilde{R}_j^p$ and $\tilde{X}_j^p$ are the raw spin-echo amplitudes from the R and X-channels for the j-th echo. The index, p=1, ..., M, denotes a particular measurement in a suite consisting of M measurements. The measurement times, $t_{j,p}$, are integral multiples of the echo spacing, i.e., $$t_{j,p} = j T E_p \text{ for } j=1, N E_p, \quad (3)$$

where $NE_p$ is the number of echoes acquired. The sum is over the $N_s$ components in the multi-exponential model where the in-phase and quadrature channel signal amplitudes are given by, $$a_{l,r} = a_l \cos \theta \quad (4a)$$

$$a_{l,x} = a_l \sin \theta, \quad (4b)$$

with θ the signal phase and $a_l$ the amplitude in the T2 distribution with relaxation time $T_{2,l}$. Note that in Eqs. (4) the signal phase does not depend on the pulse sequence parameters. This is generally valid for measurements made at the same frequency. For logging tool measurements made at different frequencies, for example, with a multi-frequency logging tool, the signal phase can vary with measurement frequency. Eqs. (4) can be modified to account for this possibility. The $N_s$ polarization functions $f_{l,p}(\xi)$ account for incomplete polarization of the signal associated with amplitudes, $a_l$, and are defined by, $$f_{l,p}(\xi) = \left(1 - \exp\left(-\frac{W_p}{\xi T_{2,l}}\right)\right), \quad (5)$$

where $W_p$ is the polarization time for the p-th measurement and ξ is an apparent T1/T2 ratio. In Eqs. (1)–(2), the random noise is assumed to be zero mean white Gaussian noise with the following statistical properties, $$\langle \tilde{N}_{j,p}^r \rangle = \langle \tilde{N}_{j,p}^x \rangle = 0, \quad (6a)$$

$$\langle \tilde{N}_{j,p}^r \tilde{N}_{k,\bar{p}}^r \rangle = \langle \tilde{N}_{j,p}^x \tilde{N}_{k,\bar{p}}^x \rangle = \Psi_p \delta_{k,j} \delta_{p,\bar{p}}, \quad (6b)$$

where angular brackets denote a statistical, or by the ergodic theorem, a time-average average over the random noise ensemble. The noise power per echo, $\psi_p$, is estimated from the raw R or X-channel data. The ringing parameters, $\Delta_{j,p}^r$ and $\Delta_{j,p}^x$, in Eqs. 1 and 2 are defined by the model, $$\Delta_{j,p}^r = \Delta_0^r + r_j^r \quad (7a)$$

and, $$\Delta_{j,p}^x = \Delta_0^x + r_j^x. \quad (7b)$$

Note that the offsets, $\Delta_0^r$ and $\Delta_0^x$, are constants (i.e., independent of time) but are allowed to be different in the R and X-channels. The transient terms, $r_j^r$ and $r_j^x$, are allowed to be arbitrary but are assumed to decay to zero after some relatively short time period (e.g., after a specified number of spin-echoes, $m_0$) such that, $$r_j^r = r_j^x \leq 0, \text{ if } j > m_0. \quad (8)$$

The ringing model specified in Eqs. (7)–(8) is consistent with the overall character of the ringing observed on laboratory data acquired by many NMR lab spectrometers and logging tools. The ringing model is shown schematically in FIG. 1. FIG. 1 shows a hypothetical ringing signal for the first 20 echoes in a CPMG where the first six echoes are corrupted by a large transient ringing signal. The R and X-Channel offsets in this example are 20 and −15 p.u., respectively. It worth noting, since it is not obvious from the plot, that all the echo amplitudes in each channel have the same offset.

A more general ringing model can be adopted by assuming that the transients and offset parameters in Eqs. (7) are measurement dependent. This situation can be treated using the method in this disclosure by introducing additional unknown ringing parameters. Justification for the model in Eqs. (7) is based on the empirical observation that the ringing parameters for many NMR instruments depend primarily on the 90 and 180-degree pulse durations in a CPMG. In such cases, the model in Eqs. (7) is appropriate for processing data suites where the measurements differ in polarization times, number of echoes acquired, and echo spacings but have the same pulse lengths.

The unknown parameters determined by fitting Eqs. (1)–(2) to the R and X-Channel spin-echo amplitudes are: (1) $2N_s$ in-phase and quadrature channel signal amplitudes, $a_{l,r}$ and $a_{l,x}$, (2) $2m_0$ in-phase and quadrature channel transient ringing parameters, $r_j^r$ and $r_j^x$, where the transient is assumed to persist for the first $m_0$ echoes in each detection channel, (3) the in-phase and quadrature channel offset parameters, $\Delta_0^r$ and $\Delta_0^x$. For pulse sequences consisting of a suite of spin-echo sequences with different polarization times, the apparent T1/T2 ratio, ξ, can also be estimated from the raw R and X-channel amplitudes.

In practice only a relatively few echoes (e.g., say the first 10 or fewer echoes) are affected by the transient ringing. According to an embodiment of the disclosed method, the user would select the value of $m_0$ based on knowledge of the character and quality of the data being analyzed or use a default value. It is understood that the above ringing model can be altered, for example, by assuming a specific analytical model for the transient decay or an offset that varies with time, without falling outside of the scope of the disclosed subject matter.

The noise power per echo, $\psi_p$, is the same in the R and X-Channels and can be estimated using the raw data from either channel. For example, using the R-channel data, $$\Psi_p \cong \frac{1}{6(NE_p - m_0 - 2)} \sum_{j=m_0+2}^{NE_p-1} (\tilde{R}_{j+1}^p - 2\tilde{R}_j^p + \tilde{R}_{j-1}^p)^2. \quad (9)$$

The above equation follows from the statistical properties of the random noise and the neglect of the signal decay that occurs between adjacent echoes. The neglect of the signal decay is valid for the relaxation times measured and echo spacings used in NMR well logging tools as well as in many other NMR applications.

Figure 2:
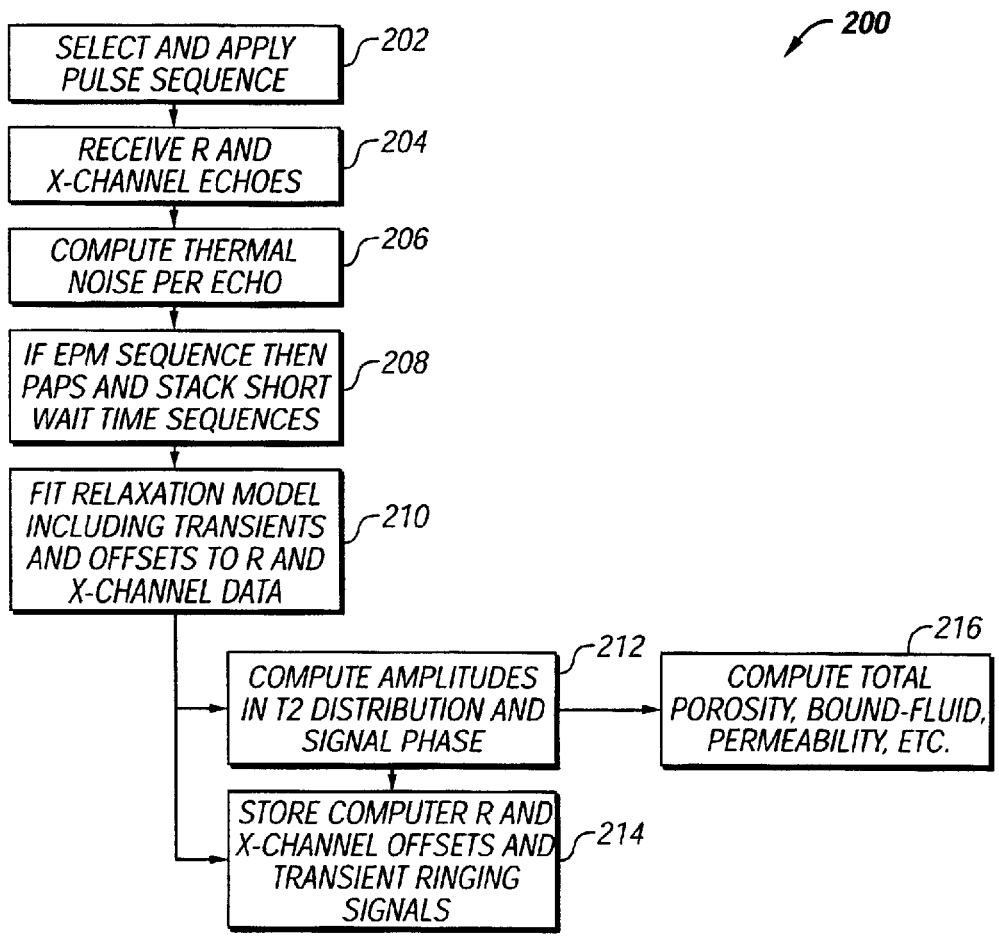
FIG. 2 is a flow diagram illustrating the steps performed in practicing the invention disclosed here.

Turning now to FIG. 2, shown is a flow diagram illustrating the steps involved in practicing the method 200 according to one embodiment of the disclosed subject matter. Specifically, NMR data is processed in the presence of noise including both transient ringing and offset noise. The process begins with selection and application of a pulse sequence at step 202 into an earth formation. The type of pulse sequence being applied is independent of the actual processing and any number of known pulse sequences or variations thereof can be utilized under the disclosed method with only minor or no modifications. At step 204 the R and X-Channel echoes from the selected acquisition are acquired. At 206 the thermal noise per echo is computed from the R and X-Channel data. Continuing at step 208, in the case of Schlumberger's EPM (McKeon et al., SPWLA Transactions, 1999) pulse sequences, short wait time pulses are combined into phase alternated pairs (PAP) and stacked (i.e., depth averaged) according to known techniques. After step 208, in the case of EPM pulse sequences, the spin-echoes consists of a CPMG acquired with a long wait time and the stacked and PAPs'ed short wait time data. At step 210 the data are processed or fit to the relaxation model appropriate to the selected pulse sequence.

The relaxation model includes the transient and offset noise contributions for the R and X-Channels. The outputs of the fitting are the NMR signal as well as the transient and offset noise parameters. According to one embodiment of the disclosed method, fitting the relaxation model to the raw spin-echo data is performed through the construction and minimization of a maximum likelihood cost function (discussed in detail below). However, once the NMR relaxation model has been developed and the raw measurements received, the model and the data may be applied or fit to one another according to any number of known methods. For example, another embodiment includes solving the set of rank deficient linear equations using singular value decomposition or maximum entropy and is understood to be within the scope of this invention. The ringing parameters and the NMR parameters are estimated by fitting the data to the relaxation model. This properly accounts for the effects of the ringing and provides accurate NMR signal parameters. A number of other known data fitting techniques that can be used to fit the data include linear or non-linear least squares, matrix inversion, and bandpass filters to remove the low frequency offsets and the high frequency transients. The latter techniques all fall within the scope of this invention.

The model may also include other components whose contribution can be characterized, such as thermal noise and other environmental effects, such as those due to temperature changes. Likewise, the model may be simplified to include less components than in the embodiments described. Such a simplification is appropriate, for example, where an operator has a high degree of confidence that a certain noise or other component is negligible, for example in the case of a low noise tool. It is also understood that in step 208 in FIG. 2 that for EPM pulse sequences short wait time data does not have to be combined into phase-alternated-pairs. That is, the method in this disclosure can be applied without combining the short wait time data into PAPs.

As is known, there are any number of processing platforms and venues, including on-site surface processing, remote surface processing or down-hole processing. It is worth noting that because the processing is performed on the raw data independent of subsequent tool measurements, real time processing may be realized during the drilling or wireline logging operation itself. However, as is known, the raw data may be stored for processing at a later time.

The outputs determined from the model-data fitting operation, according to one embodiment are the amplitudes in the T2 distribution and the signal phase output at step 212, and the transient ringing and offset parameters output at step 214. From the amplitudes in the T2 distribution, porosity, bound-fluid, permeability, etc. are computed at step 216. These processes are described in more detail below. In addition to T2 determinations, it will be understood that the disclosed processing techniques can be applied with little or no modification to other NMR pulse sequences such as, for example, the inversion recovery sequence for T1 determination or fluid characterization sequences (Freedman, U.S. Pat. No. 6,229,308 B) for determining fluid volumes, saturations, and oil viscosity.

The unknown parameters can be determined using the window processing method of Freedman (U.S. Pat. No. 5,291,137), fully incorporated herein by reference, by minimization of the maximum likelihood function, $$-\ln L = \sum_{p=1}^{M} \left\{ \sum_{m=1}^{N_w} \frac{\left(\tilde{I}_{m,p}^r - \sum_{l=1}^{N_s} a_{l,r} F_{m,p}(T_{2,l}) f_{l,p}(\xi) - \Delta_{m,p}^r \hat{\sigma}_{m,p}^2\right)^2}{2\Psi_p \hat{\sigma}_{m,p}^2} + \sum_{m=1}^{N_w} \frac{\left(\tilde{I}_{m,p}^x - \sum_{l=1}^{N_s} a_{l,x} F_{m,p}(T_{2,l}) f_{l,p}(\xi) - \Delta_{m,p}^x \hat{\sigma}_{m,p}^2\right)^2}{2\Psi_p \hat{\sigma}_{m,p}^2} + \frac{\gamma_p}{2\Psi_p} \sum_{l=1}^{N_s} a_l^2 \right\}. \quad (10)$$

In the above maximum likelihood function the following functions and parameters have been defined. The R-channel echo window sums, $$\tilde{I}_{m,p}^r,$$

are defined by, $$\tilde{I}_{m,p}^r = \sum_{j=N_m+P_m}^{N_{m+1}} \tilde{R}_j^p, \quad (11)$$

and similarly for $$\tilde{I}^x_{m,p}.$$

The limits in the summations are the integers, $N_m$ and $N_{m+1}$, that define the echo endpoints of the m-th window and where, $\rho_m=1-\delta_{m,1}$. The sensitivity functions in Eq. (10) are defined by the summations, $$F_{m,p}(T_{2,l}) = \sum_{j=N_m+\rho_m}^{N_{m+1}} \exp\left(-\frac{jTE_p}{T_{2,l}}\right). \quad (12)$$

The number of echoes in the m-th window is defined by, $$\hat{\sigma}^2_{m,p} = N_{m+1} - N_m + \delta_{m,1}. \quad (13)$$

The smoothing or regularization parameters, $\gamma_p$, are used to select smooth T2 distributions that are consistent with the measured data. Specifically, it is well-known to those skilled in the art that without a smoothing function or constraint, there are an infinite number of solutions that will fit the data because the inversion problem is ill-conditioned. This and other smoothing or regularization conditions and parameters are well known in the industry and can be applied within the scope of this invention.

The minimization of a maximum likelihood function like the one in Eq. (10) with respect to the parameters in the relaxation model can be achieved using, for example, the algorithm discussed in U.S. Pat. No. 6,229,308 B1 issued to Freedman, hereby fully incorporated by reference. The minimization of the function in Eq. (10) simultaneously fits the R and X-channel data to the NMR and ringing model. The amplitudes in the T2 distribution are obtained from the R and X-channel amplitudes determined from the minimization by using the equations, $$a_l = \sqrt{a_{l,r}^2 + a_{l,x}^2}, \quad (14)$$

for l=1, . . . , $N_s$. Thus, the disclosed technique provides improved NMR logging measurements which eliminate the offset and transient noise contributions without the need for PAP ringing elimination methods.

The relaxation or noise model is applied directly to the raw data obtained with a single CPMG or a suite of CPMGs, or suites containing both CPMGs and PAP data. This in turn eliminates the need for a subsequent application of the second half of the phase alternated pair and the associated long wait time. Ultimately, improved vertical resolution or alternatively increased logging rates are realized compared to that observed for PAP techniques. Specifically, due to elimination of the second half of the PAP wait time and the associated tool travel time during that time, vertical resolution is reduced by half or logging speed can be doubled for the same vertical resolution as provided by processing a complete PAP. It is understood that the method can be applied to a variety of pulse sequences commonly used in NMR well logging. For example, in Schlumberger's Enhanced Precision Mode (EPM), discussed earlier with reference to FIG. 2, the pulse sequence consists of a CPMG with a long wait time followed by multiple short wait time sequences that are acquired as phase-alternated-pairs.

The disclosed method is also readily applied to processing these data without the need to combine this sequence with a following sequence where the CPMG is acquired with opposite phase. Specifically, for PAPs sequences, a purpose of the second phase alternated CPMG is to provide cancellation of the offset in the preceding CMPG. Because the relaxation model of the disclosed processing method takes care of noise compensation, there is no need to combine a CPMG with other CPMGs which degrades vertical resolution because of the movement of the logging tool. That is, the method of this disclosure can be applied to only the first half of the standard EPM pulse sequence. This provides for EPM measurements with higher vertical resolution or increased logging speed. Similarly, the method can be applied to more sophisticated sequences designed for measuring hydrocarbon volumes, saturations, and oil viscosity (Freedman, U.S. Pat. No. 6,229,308 B1). The method is also applicable to removing the effects of ringing from PAPs data that often contain residual ringing because of imperfect cancellation of the offsets. It should be known by those skilled in the art that the method can be applied to NMR pulse sequences other than CPMG sequences to eliminate ringing that contaminates the NMR signal.

The formation porosity and other properties such as the bound and free-fluid porosities and permeability can be computed directly from the amplitudes in the T2 distribution as disclosed in U.S. Pat. No. 5,291,137 to Freedman. For example, the porosity is proportional to the sum of the amplitudes, i.e., $$\varphi = K \sum_{l=1}^{N_s} a_l \quad (15)$$

where K is a factor containing calibration and environmental factors. The bound and free-fluid porosities are obtained by partitioning the above sum into two parts using empirically determined cutoffs. The signal phase can also be estimated from the R and X-channel amplitudes, e.g., $$\theta = ATAN2D\left(\sum_{l=1}^{N_s} a_{1,x}, \sum_{l=1}^{N_s} a_{1,r}\right). \quad (16)$$

ATAN2D is the 4-quadrant inverse tangent FORTRAN function that is defined such that, $-180 \leq \theta \leq 180$. Typically, for PAP applications, the signal phase is determined as an initial matter once the ringing has been minimized. However, without the second half of the PAP, according to the disclosed technique, the phase angle cannot be determined until after the signal amplitudes are determined. Specifically, the phase angle information can be determined directly from the raw data without the need for further tool operations.

According to an embodiment, the NMR processing can be performed independent of downhole operations once the data has been retrieved. For example, according to one embodiment, raw data may be processed downhole or transmitted to a surface processor concurrent with the borehole operations to obtain real time interpretation of the raw data. As is known, borehole operations may include while drilling operations as well as wireline operations occurring after the drill string has been removed from the borehole. Alternatively, the disclosed processing can be performed based on certain operating conditions or formation evaluation objectives. Specifically, a relaxation model may be selected based on initial logging objectives or conditions then modified during the the logging operation to account, for example, for changes in operating conditions or changes in formation evaluation objectives. In one embodiment, the relaxation model representation of the noise contribution is modified during station logging operations rather than logging while the tool is in motion. In another embodiment, a change of formation evaluation objectives such as performing high resolution measurements results in a modification to the relaxation model to account for the expected change in the returned NMR signal. Similar modifications to the relaxation model may be performed during the downhole operations for other changes to the measurement pulse sequences.

According to another embodiment, processing may occur subsequent to obtaining the data. Further, processing according to the disclosed method may be performed on data obtained using various retrieval methods, including PAP and other acquisitions. Specifically, in circumstances where data obtained from a PAP acquisition results in noisy data, the PAP'ed data can be processed according to the present methods to obtain further noise minimized data.

The disclosed method can be used to process NMR well logging data acquired as single raw CPMGs and therefore can be used to obtain high resolution logs of formation NMR properties (e.g., T2 distributions, total porosity, bound and free-fluid porosity, permeability, etc.) at higher vertical resolution than those obtained by standard processing of PAP data. This is graphically shown in FIG. 3 with the porosity log obtained by processing single raw CPMGs (no depth stacking) acquired by a CMR tool in a Schlumberger test well. Also shown for comparison is the porosity log obtained using the commercial TCMR processing (see Freedman et al. in paper OO presented at the 1997 SPWLA meeting) on single sequential PAPs. The CPMG processing has higher vertical resolution and also provides accurate porosity in spite of the fact that the raw CPMG spin-echo amplitudes exhibit ringing. The higher resolution of the porosity from the CPMGs (solid line) is manifested by the faster rise and fall of the porosities at the bed boundaries compared to the data obtained from PAP data (dotted line).

Figure 3:
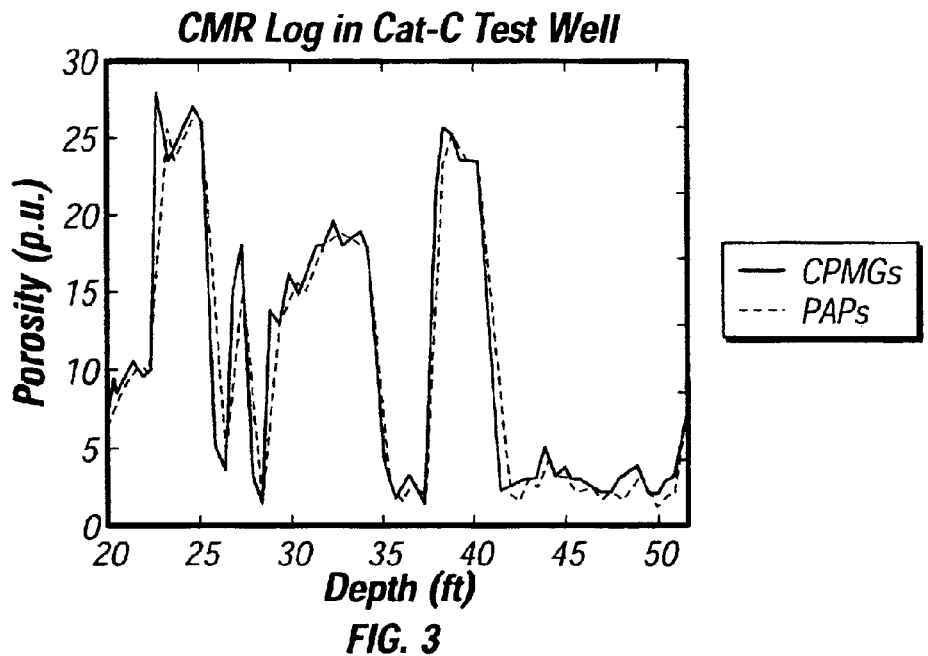
FIG. 3 compares a porosity log computed from a single CPMG according to the disclosed subject matter with one from processing phase alternated pairs (PAP) of CPMGs.
Figure 4:
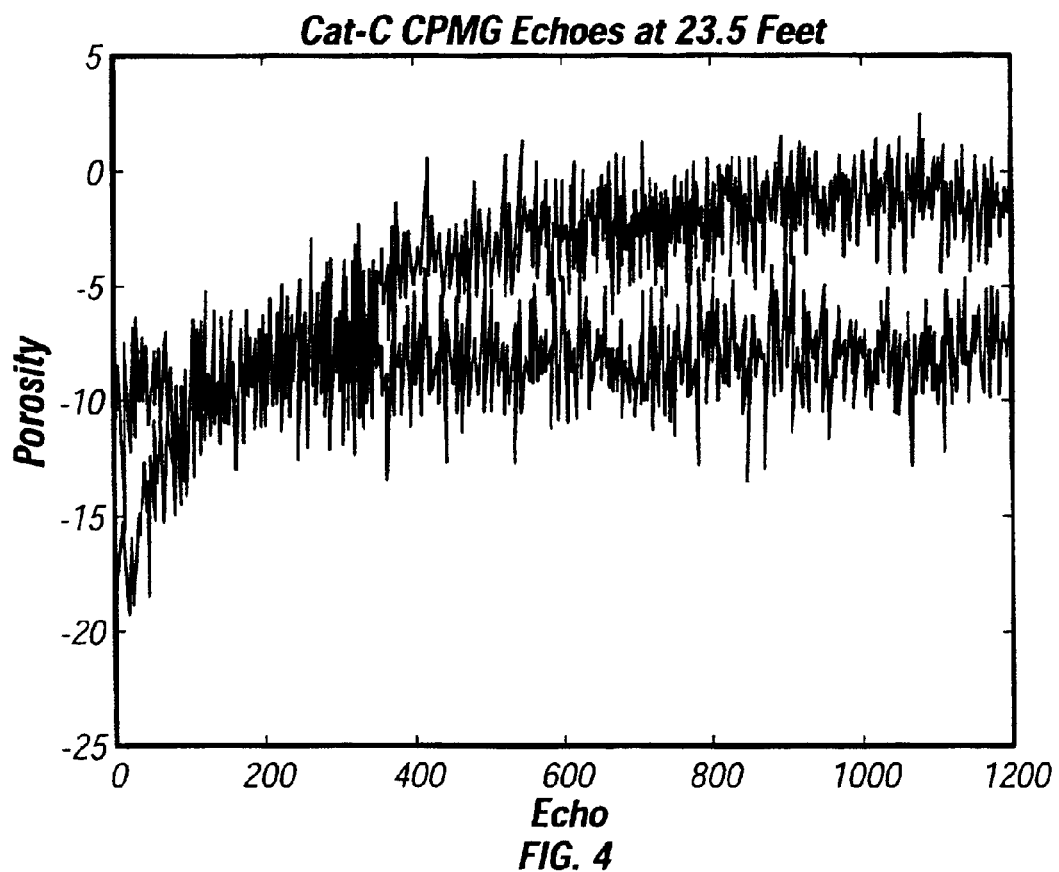
FIG. 4, shows R and X-channel spin-echoes from a single CPMG with an obvious offset in the R-channel data.
Figure 5:
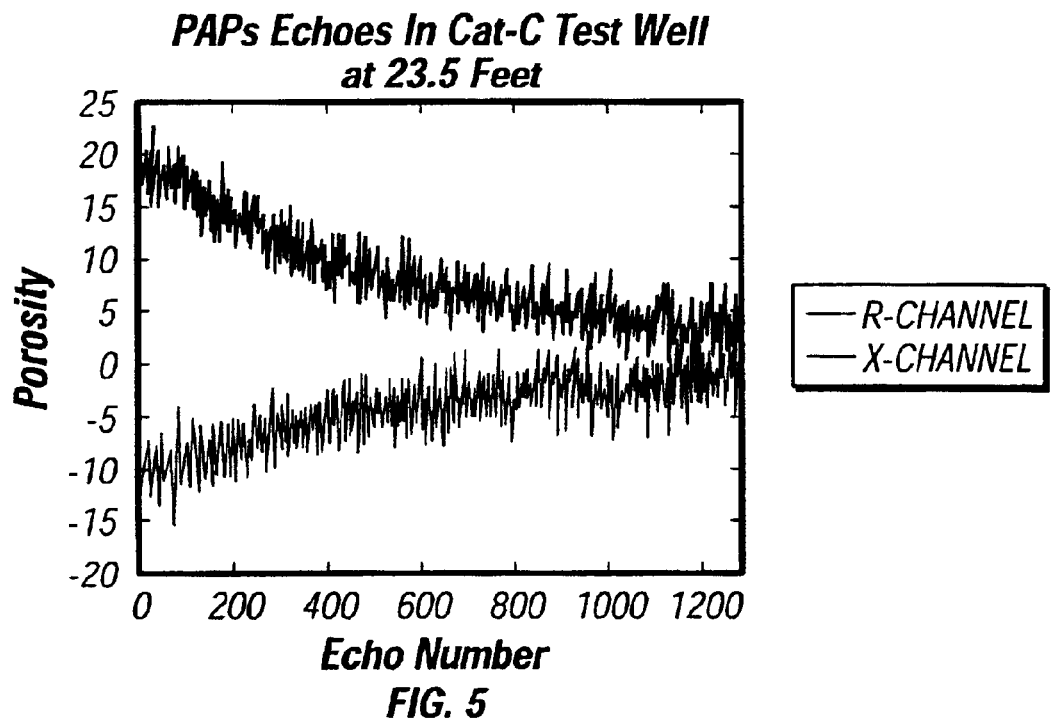
FIG. 5, shows R and X-channel spin-echoes from a phase-alternated-pair (PAP) of CPMGs with cancellation of the offsets.

Turning to FIG. 4, illustrated is an example of an offset in the R-Channel data for a CPMG acquired at a well depth of 23.5 feet in the test well data of FIG. 3. The variations about the mean signal value for each channel is thermal noise which is always present. The thermal noise can be considered to be a zero mean value which averages to zero over the CPMG acquisition time. The offset can be seen when the R-Channel data (dark line) is compared to the X-Channel data (light line). While the X-Channel data relaxes toward zero, indicating little offset, the R-Channel, due to the phase angle, exhibits no early spin echo signal contribution and remains constant across the depth range. Since it is obvious no NMR signal is present in the R-Channel because no relaxation is exhibited, the non-zero value of the R-Channel is solely due to the offset. By comparison no offsets are present in the sequential PAPs data shown in FIG. 5.

Figure 6:
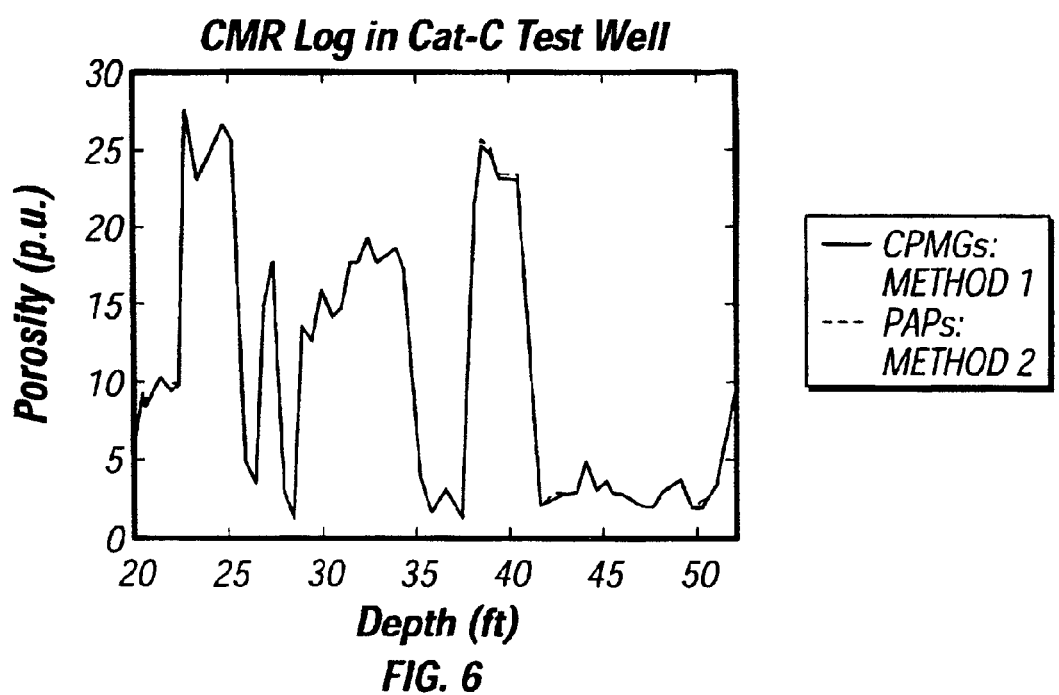
FIG. 6, porosity logs computed from single CPMGs using two different implementations of the invention disclosed here.

Another embodiment according to the disclosed method for processing ringing NMR data is to solve the problem in sequential steps using a reduced version of the likelihood function in Eq. (10). First, a fit is calculated for only the R-channel data and solved for the amplitudes, $a_{l,r}$ and the R-channel ringing parameters. Then, a fit is calculated for the X-channel data amplitudes, $a_{l,x}$, and the X-channel ringing parameters. This method (referred to as method 2 in FIG. 6) reduces the number of unknown model parameters that are fit in the minimization at each step, however, the two methods yield virtually identical results as shown in FIG. 6. FIG. 6 illustrates porosity logs obtained by processing raw CPMGs acquired by a CMR tool in the CAT-C Test Well. The porosity logs are obtained using the two embodiments described above. Note that both methods yield virtually identical results.

Further, although the embodiments discussed above are primarily directed to an new independent ringing elimination technique, it should be understood that the disclosed methods may be performed or combined with existing ringing elimination approaches to further improve noise reduction. For example, these methods can be performed with only minor modifications to existing PAP data that, due to imperfect cancellations, contains uncorrected ringing signals.

The disclosed methods provide processing techniques that improve NMR measurement interpretation by eliminating the effect of transient ringing and offsets in the raw NMR data. Specifically, raw NMR data are fit to a mathematical relaxation model that includes both coherent noise components and the actual NMR signal. The coherent noise components are further broken into offsets and transient ringing components, which are then computed along with the NMR signal outputs.

What is claimed is:

1. A method for interpreting data obtained from nuclear magnetic resonance measurements of formations surrounding an earth borehole, comprising: receiving a set of data comprising at least a portion of the nuclear magnetic resonance measurements; defining a set of variables representing a relaxation model for estimating a noise contribution associated with the nuclear magnetic resonance measurements, the relaxation model comprising a coherent noise component; and calculating a nuclear magnetic resonance signal output based on the set of data and the relaxation model, the nuclear magnetic resonance signal output being compensated for the noise contribution.

2. The method of claim 1, the relaxation model further comprising:

a nuclear magnetic resonance relaxation signal component.

3. The method of claim 2, the coherent noise component further comprising:

an offset component; and a time-dependent transient component.

4. The method of claim 1, wherein the set of data is received from a first quadrature data channel and a second in-phase data channel.

5. The method of claim 4, wherein the nuclear magnetic resonance signal outputs are calculated independently for each data channel.

6. The method of claim 4, wherein the nuclear magnetic resonance signal outputs are calculated for each data channel in a sequential manner.

7. The method of claim 4, wherein the nuclear magnetic resonance signal outputs are calculated simultaneously for both data channels.

8. The method of claim 1, wherein the calculating step is performed according to a mathematical data fitting operation to calculate the nuclear magnetic resonance signal output.

9. The method of claim 8, wherein the data fitting operation is a maximum likelihood cost function.

10. The method of claim 1, wherein the set of data is raw data without noise compensation.

11. The method of claim 10, wherein the nuclear magnetic resonance signal output is calculated directly from the raw data.

12. The method of claim 1, wherein the data set comprises:

a coherent noise component; and a nuclear magnetic resonance signal relaxation component.

13. The method of claim 1, wherein the nuclear magnetic resonance signal output includes an estimation of hydrocarbon properties and saturation.

14. The method of claim 1, wherein the nuclear magnetic resonance signal output includes a distribution of transverse relaxation values.

15. The method of claim 1, wherein the nuclear magnetic resonance signal output includes a distribution of longitudinal relaxation values.

16. A method for obtaining in a borehole a nuclear magnetic resonance measurements of formations surrounding the borehole in the presence of a noise contribution, comprising the steps of: applying a sequence of pulses to the formation surrounding the borehole; receiving nuclear magnetic resonance measurements in response to the sequence of pulses; defining a set of variables representing a relaxation model for estimating a noise contribution associated with the nuclear magnetic resonance measurements, the relaxation model comprising a coherent noise component; and computing a nuclear magnetic resonance signal output based on the relaxation model and a set of data comprising at least a portion of the nuclear magnetic resonance measurement; the nuclear magnetic resonance signal output being compensated for the noise contribution.

17. The method of claim 16, further comprising the step of:

repeating the steps of applying receiving and computing during a borehole logging operation.

18. The method of claim 16, the relaxation model further comprising:

a nuclear magnetic resonance signal relaxation component.

19. The method of claim 16, coherent noise component further comprising:

an onset component; and a time-dependent transient component.

20. The method of claim 16, wherein the set of data is received from a first quadrature data channel and a second in-phase data channel.

21. The method of claim 20, wherein the nuclear magnetic resonance signal output and the noise contribution are computed independently for each data channel.

22. The method of claim 20, wherein the nuclear magnetic resonance signal outputs are calculated for each data channel in a sequential manner.

23. The method of claim 20, wherein the nuclear magnetic resonance signal outputs are calculated simultaneously for both data channels.

24. The method of claim 16, wherein the calculating step is performed according to a mathematical data fitting operation to compute the nuclear magnetic output.

25. The method of claim 24, wherein the data fitting operation is a maximum likelihood function.

26. The method of claim 16, wherein the set of data is raw data without noise compendation.

27. The method of claim 26, wherein the nuclear magnetic resonance signal output is calculated directly from the raw data.

28. The method of claim 16, the data set comprises:

a coherent noise component; and a nuclear magnetic resonance relaxation component.

29. The method of claim 16, wherein the nuclear magnetic resonance signal output includes an estimation of hydrocarbon properties and saturation.

30. The method of claim 16, wherein the nuclear magnetic resonance signal output includes a distribution of transverse relaxation values.

31. The method of claim 16, wherein the nuclear magnetic resonance signal output includes a distribution of longitudinal relaxation values.

32. The method of claim 16, further comprising the step of:

adjusting the relaxation model based on operating conditions.

33. The method of claim 14, further comprising the step of:

adjusting the relaxation model based on formation evaluation objectives.

34. The method of claim 16, further comprising the step of:

adjusting the relaxation model based on a data acquisition sequence.

* * * * *